United States Patent [19]
Garris

[11] 3,942,900
[45] Mar. 9, 1976

[54] QUALITY CONTROL MONITOR FOR MEDICINAL CAPSULE PACKAGING APPARATUS
[75] Inventor: Charles R. Garris, Stratford, N.J.
[73] Assignee: SmithKline Corporation, Philadelphia, Pa.
[22] Filed: June 6, 1974
[21] Appl. No.: 477,160

Related U.S. Application Data
[62] Division of Ser. No. 363,346, May 24, 1973, Pat. No. 3,882,316.

[52] U.S. Cl. .............................. 356/237; 250/578
[51] Int. Cl.² ......................................... G01N 21/32
[58] Field of Search ........ 250/221, 223 R, 224, 578; 209/111.5, 111.7; 356/209, 212, 237, 240

[56] References Cited
UNITED STATES PATENTS

| | | | |
|---|---|---|---|
| 3,555,287 | 1/1971 | Schmermund | 250/223 |
| 3,709,598 | 1/1973 | Vandenberg et al. | 356/237 X |
| 3,756,402 | 9/1973 | Wagers et al. | 209/111.7 X |
| 3,757,943 | 9/1973 | Chae et al. | 356/240 X |
| 3,814,931 | 6/1974 | Kuroda | 250/233 R |

Primary Examiner—Alfred E. Smith
Assistant Examiner—F. L. Evans
Attorney, Agent, or Firm—Smith, Harding, Earley & Follmer

[57] ABSTRACT

Medicinal capsules which are secured by machine to a backing strip are photoelectrically inspected by multiple pairs of light sources and detectors specially arranged so as to permit the simultaneous inspection of a number of closely spaced capsules arranged in a row. The extent to which a capsule is filled is determined by the time interval during which a light beam is blocked by the capsule contents. This interval is electrically compared with a standard time interval. After the backing strip is cut into separate cards, each carrying several capsules, the electrical comparison means effects rejection of any card containing an unsatisfactory capsule. Further means are provided for similarly rejecting cards having badly misaligned capsules. Should the apparatus sense an excessive number of unsatisfactory cards, the packaging machinery is automatically shut down. Electrical means are provided for adjusting the delay between the sensing of an unsatisfactory capsule or row of capsules and the mechanical rejection of a card in order to effect optimum operation.

3 Claims, 10 Drawing Figures

QUALITY CONTROL MONITOR FOR MEDICINAL CAPSULE PACKAGING APPARATUS

CROSS REFERENCE TO RELATED APPLICATION

This is a division of my application, Ser. No. 363,346, filed May 24, 1973 and now U.S. Pat. No. 3,882,316.

SUMMARY OF THE INVENTION

This invention relates to quality control monitoring, and particularly to a quality control monitor especially adapted for use in conjunction with an apparatus for packaging medicinal capsules and the like.

Medicinal capsules, for example the well known CONTAC decongestant capsules, are frequently packaged in a manner such that the capsules are secured to a backing strip by means of a sheet of transparent thermoplastic material which is heat-sealed to the card so as to form individual pockets for the capsules. In a typical packaging machine, capsules are delivered through a group of parallel tubes to the point at which the thermoplastic sheet is secured to a backing strip to provide the aforementioned pockets. The capsules are fastened to the moving backing strip in rows which are transverse to the direction of movement of the backing strip. After the backing strip moves past the point at which the rows of capsules are secured to it, it is automatically cut into cards, each card carrying one or more rows of capsules.

Heretofore, the cards, after cutting, were carried by a conveyor to a delivery location at which they were collected. A visual inspection was made by one or more operators located along the path of the conveyor. A card which an operator deemed unsatisfactory, because of a partially filled capsule, a missing capsule, or a badly misaligned row of capsules would be manually removed from the conveyor. Visual inspection is obviously costly and tedious. It is also unreliable because it is difficult to judge whether or not a capsule is adequately filled by a quick visual inspection. Visual inspection is made still less reliable by tinted capsule material, which often renders the capsule contents almost invisible.

Automatic inspection means are provided in accordance with this invention, having among its objects the following.

A first object of the invention is to provide automatic optical inspection means which is capable of inspecting capsules which are closely spaced in rows arranged on and transverse to the direction of movement of an opaque, reflective backing strip. This object is accomplished by arranging light beam producing means and photosensitive detectors in pairs for the simultaneuos inspection of the capsules in a row, so that each beam approaches the backing strip at an oblique angle and is reflected to a different one of the detectors and so that each plane defined by the approaching and reflecting part of a beam intersects the plane defined by the movement of a row of capsules to define a line which is oblique with respect to the direction of motion of the row of capsules. With the light beam producing means and the photosensitive detectors so arranged, the beam is able to pass through the capsule in a direction transverse to the capsule's long dimension, and is therefore capable of making a more accurate determination of the amount of medication in a capsule than would be possible if the beam passed through the capsule in the longitudinal direction. However, with the arrangement described, the light beam producing means and photosensitive detectors do not physically interfere with each other even though they are capable of simultaneously inspecting capsules which are closely spaced with respect to each other in rows.

A second important object of the invention is the accurate and consistent determination of whether or not a capsule meets the criteria for acceptability. In accordance with the invention, this is accomplished by automatically comparing an electronically established time interval with the interval during which an inspection beam is blocked by the capsule contents. If any capsule on a card fails to meet the criteria for acceptance, a reject mechanism is activated to effect delivery of the card to a reject location.

Another object of the invention is to insure that the capsules in a row are satisfactorily aligned with each other. As the contents of each capsule clears the inspection beam, assuming the capsule is filled satisfactorily, a pulse is produced. The corresponding pulses for all of the capsules in the row must overlap in order for the apparatus to determine that satisfactory alignment exists. This is accomplished by the use of a coincidence gate. The criteria for proper alignment may be adjusted by adjusting the pulse lengths. In addition, the apparatus insures that each row of capsules is positioned within certain limits measured in the direction of backing strip movement by means of a clock pulse, synchronized with the packaging mechanism, and with which the aforementioned predetermined pulses must all coincide.

The packaging machinery, equipped with the quality control monitor may be operated unattended for extended periods of time. Nevertheless, it is possible for the packaging machinery to break down so that it produces unacceptable cards with great frequency. Another object of the invention is to effect shutdown of the packaging apparatus when the occurrence of unacceptable cards become so frequent as to indicate that continued operation of the machine would result in a large amount of waste. This determination is preferably accomplished by the use of a shift register in conjunction with gating circuitry to determine if a predetermined number of successively produced cards are unacceptable. The predetermined number may be adjusted by the operator.

A still further object of the invention is to optimize the operation of the rejection means. This is accomplished by the production of a rejection pulse at an appropriate time determined by the shift register. This also may be adjusted by the operator to insure rejection of all unacceptable cards.

Various other objects will be apparent from the following description.

DETAILED DESCRIPTION

Figure 1:
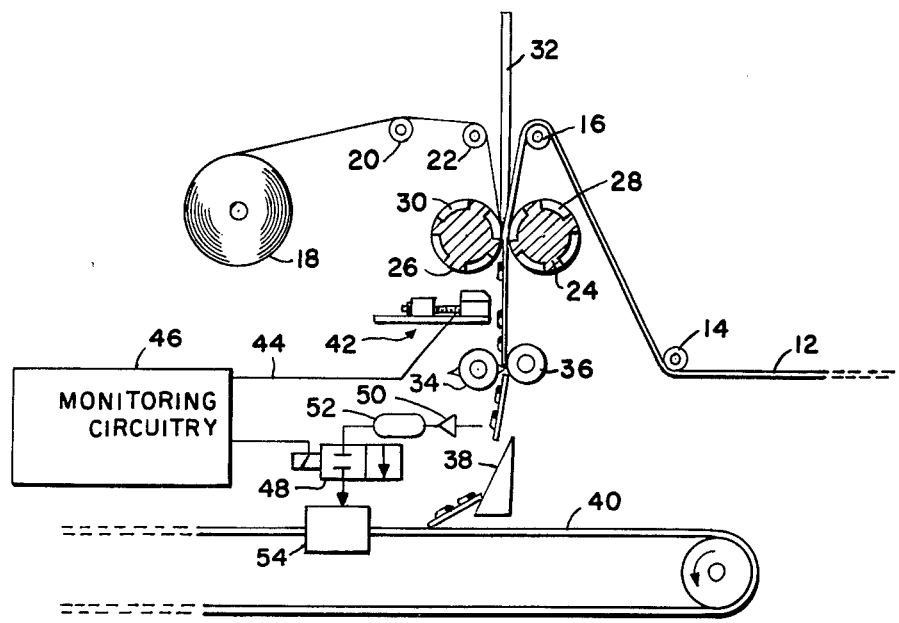
FIG. 1 is a diagrammatic view of a capsule packaging machine equipped with a quality control monitor in accordance with the invention.

FIG. 1 shows the basic elements of a capsule packaging machine and the relationship to it of the quality control monitor in accordance with the invention.

A continuous backing strip 12, preferably of cardboard having a reflective white surface, is fed around a series of guide rollers including rollers 14 and 16 preferably at a substantially constant speed. A heat-sealable thermoplastic material such as polyvinyl chloride is fed from a supply roll 18 over rollers 20 and 22. The backing strip and the thermoplastic sheet are brought together between a pair of heated die rollers 24 and 26, which, by heating, seal the thermoplastic sheet of the backing strip. The die rolls are provided with pockets, typical pockets being indicated at 28 and 30. These pockets provide clearance which allows capsules to be inserted between the backing strip and the thermoplastic sheet through a bank of tubes, the tube on the near end of the bank being indicated at 32. The die rolls effect heat sealing so as to form pockets which secure the capsules in place in rows on the backing strip, the rows being transverse to the direction of movement of the backing strip. Each pocket is heat-sealed around its entire periphery.

A bladed roller 34 and a backing roller 36 effect cutting of cards from the backing strip which slide down incline 38 onto conveyor 40 which normally delivers the cards to a delivery location.

Figure 2:
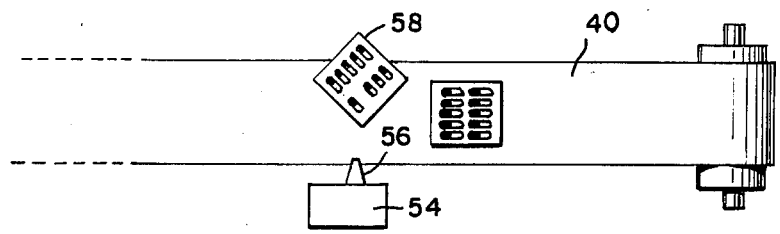
FIG. 2 is a plan view of the conveyor and card rejection mechanism in accordance with the invention.

The quality control monitor comprises an optical inspection head 42 which is connected through cable 44 to monitoring circuitry 46. The monitoring circuitry effects control of a solenoid valve 48 which controls the flow of air from compressor 50 and reservoir 52 to a reject mechanism 54. Reject mechanism 54 is positioned alongside the conveyor and is provided with a nozzle 56 (FIG. 2) which is located just above the conveyor surface whereby a blast of air delivered through the nozzle is able to effect movement of an unacceptable card such as 58 to a reject location. The principal function of the monitoring circuitry 46, as will be explained more fully, is to establish and apply predetermined criteria for acceptance or rejection of a card and to effect rejection of unacceptable cards at the proper time as they pass nozzle 56 of reject mechanism 54.

Figure 3:
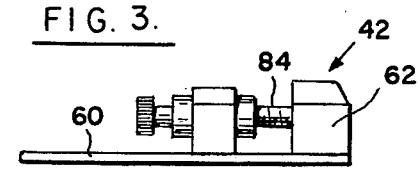
FIG. 3 is a side elevation of a capsule inspection head.
Figure 4:
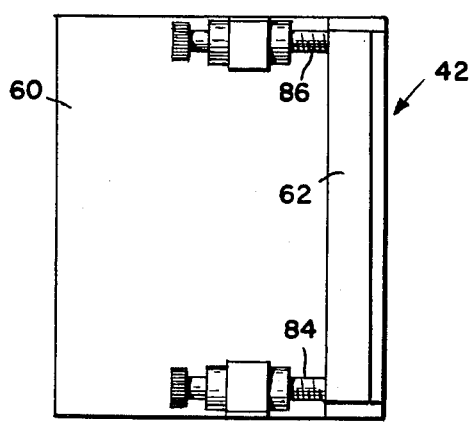
FIG. 4 is a top plan view of the capsule inspection head.

FIGS. 3–8 show the optical inspection head 42 in detail. As shown in FIGS. 3 and 4, the inspection head comprises a mounting plate 60 on which is secured a block 42 in which there is provided an array of cylindrical passages for mounting light beam producing means and photosensitive detectors.

Figure 5:
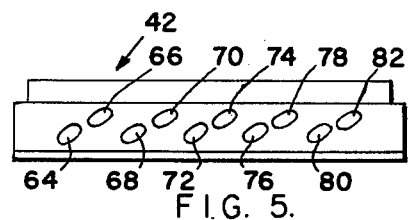
FIG. 5 is an elevation of the inspection head viewed from the capsule side.
Figure 6:
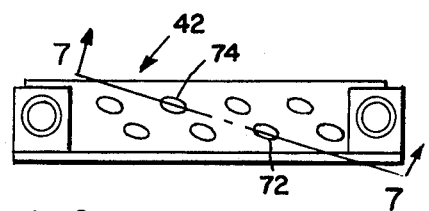
FIG. 6 is an elevation of the capsule inspection head viewed from the side opposite the capsule side.
Figure 7:
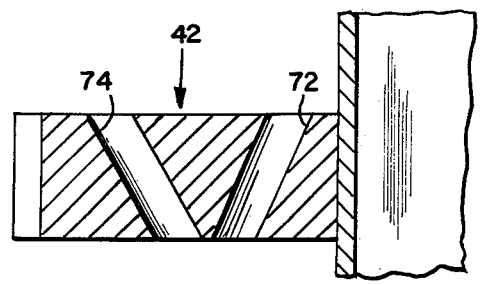
FIG. 7 is a section of the inspection head taken on the plane indicated at 7—7 in FIG. 6.

The cylindrical passages are specially arranged so as to permit the simultaneous inspection of a number of closely spaced capsules arranged in a row. In particular, the cylindrical passages are arranged in pairs so that, as shown in FIG. 5, passages 64 and 66 constitute a first pair, 68 and 70 constitute a second pair, 72 and 74 constitute a third pair, 76 and 78 constitute a fourth pair, and 80 and 82 constitute a fifth pair.

Figure 8:
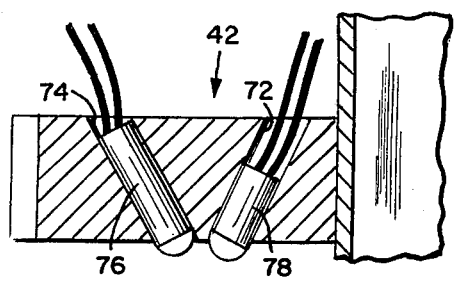
FIG. 8 is a sectional view similar to FIG. 7, showing a light beam producing means and a photosensitive detector mounted in the inspection head.

One passage in each pair is used to mount a light beam producing means such an incandescent lamp 76 shown mounted in cylindrical passage 74 in FIG. 8. The other passage in a pair is used to mount a photosensitive detecting means such as phototransistor 78 shown mounted in cylindrical passage 72 in FIG. 8. The axis of each cylindrical passage in a pair intersects the axis of the other cylindrical passage in the pair so that the planes defined by the intersecting axes intersect a plane defined by the movement of a row of capsules past the inspection head to define lines which are oblique with respect to the direction of motion of the row of capsules. The beam produced by the light beam producing means is aligned with the axis of the cylindrical passage in which the beam producing means is mounted. Therefore, it is apparent that each beam approached the backing strip at an oblique angle and is reflected to a different one of the detectors in the array so that each plane defined by the part of the beam approaching the backing strip and the part of the beam reflected by the backing strip intersects the plane defined by the movement of a row of capsules to define a line which is oblique with respect to the direction of motion of the row of capsules.

The aforementioned oblique relationship allows the light beam producing means and photosensitive detectors to be accommodated in a relatively small row-wise space without interfering with each other, and thus allows the simultaneous inspection of a large number of capsules which are closely spaced in a row.

Returning to FIGS. 3 and 4, screws 84 and 86 permit adjustment of the distance between block 62 and the backing strip to obtain optimum reflection of the inspection beams back to their corresponding photosensitive detectors.

Figure 9:
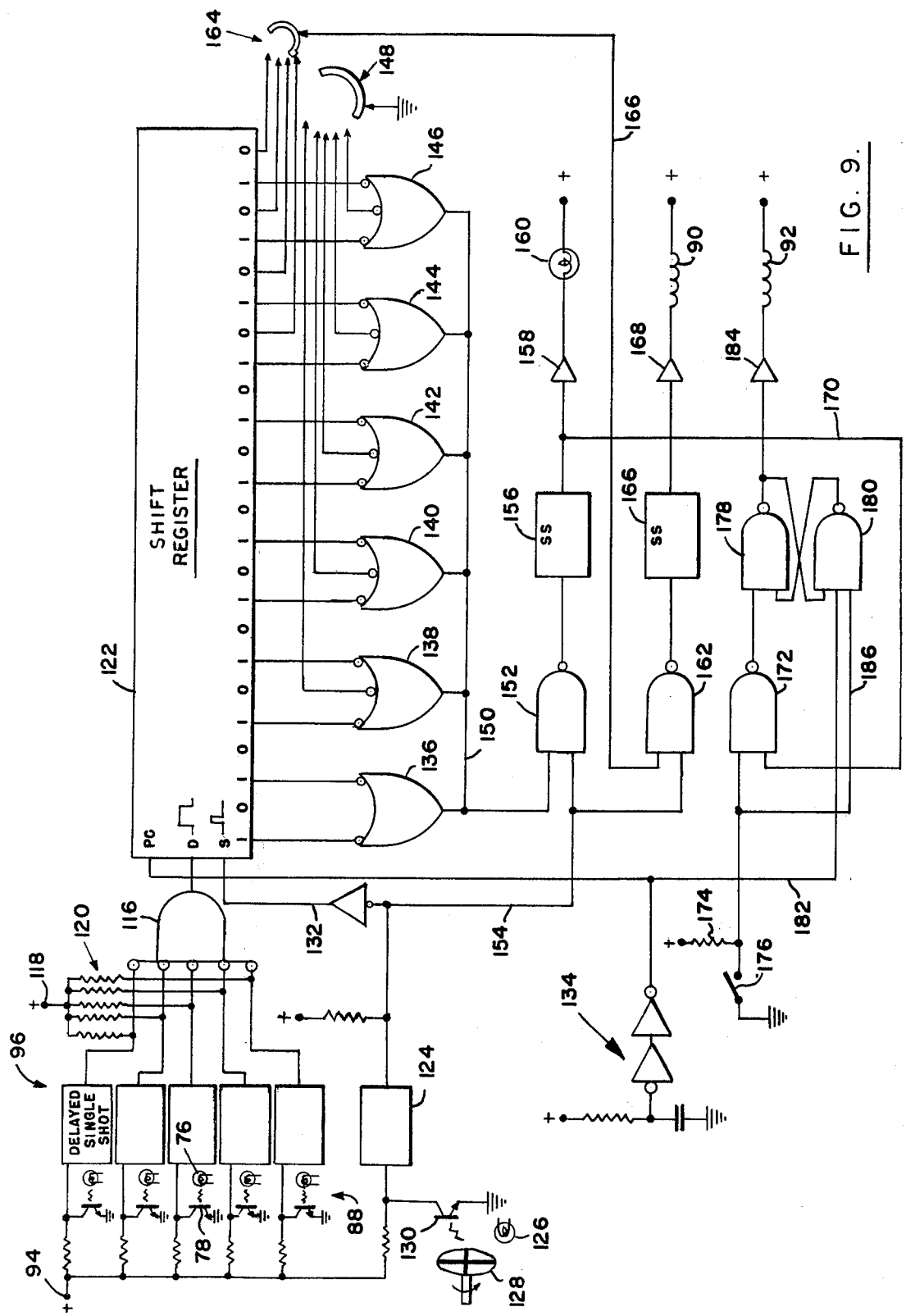
FIG. 9 is a schematic diagram of the electrical circuitry associated with the quality control monitor.

FIG. 9 shows the monitor circuitry which receives outputs from the array of light beam producing means and photosensitive means indicated generally at 88, and automatically effects operations of solenoid 90 of solenoid valve 48 (FIG. 1) to effect card rejection, and which also automatically operated a solenoid 92 to cause the capsule packaging machinery to halt when the occurrence of unacceptable cards becomes too frequent.

Each phototransistor in array 88 acts as a gate allowing delivery, when the light beam approaching it is blocked, of a positive signal from positive supply terminal 94 to the input of a delayed single shot multivibrator in group 96, which consists of five such multivibrators, there being one for each phototransistor in the array.

The function of the delayed single shot multivibrator is to establish a standard time interval, to compare the standard time interval with the duration of the positive signal provided when the contents of a capsule block the light beam which normally impinges on the associated phototransistor, and to provide an output pulse when the duration of the applied pulse exceeds the standard time interval, the output pulse commencing at the end of the standard time interval. In other words, the delayed single shot multivibrator provides its output pulse when the duration of the input pulse exceeds a predetermined limit.

Figure 10:
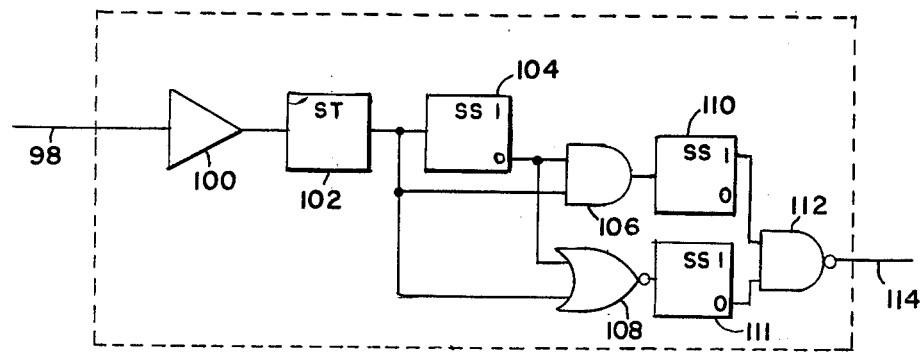
FIG. 10 is a schematic diagram of a delayed single shot multivibrator, several of which are used in the circuit of FIG. 9.

The internal details of a single delayed single shot multivibrator are illustrated in FIG. 10. The positive pulse produced by the blocking of the light beam to a phototransistor is applied at line 98 to the input of amplifier 100, the output of which is delivered to a Schmitt trigger 102. The output of the Schmitt trigger is delivered to the input of an ordinary single shot (or monostable) multivibrator 104, to one of the inputs of AND gate 106, and to an input of OR gate 108. The "0"output of single shot multivibrator 104 (which output is normally high) is connected to the other input of AND gate 106 and to the other input of OR gate 108. The output of AND gate 106 is connected to the input of a second single shot multivibrator 110, and its "1"output (which is normally low) is delivered to one of the inputs of AND gate 112. The output of OR gate 108 is negated and delivered to the other input of a third single shot multivibrator 111. The "0"output of multivibrator 111 is delivered to the other input of AND gate 112. The output of AND gate 112 is negated and delivered at output line 114.

In operation, multivibrator 104 determines the predetermined time interval with which the duration of the applied pulse is compared. Multivibrator 110 determines the duration of the output pulse if an output pulse is produced for a given input pulse. Multivibrator 111 primes gate 112 for coincidence with the output of multivibrator 110, and inhibits the output at line 114, if the input pulse is interrupted. The time constants of multivibrators 104, 110 and 111 are preferably adjustable so that their output pulse lengths may be varied.

Suppose, for example, that a pulse is applied at line 98 which has a duration shorter than the delay of multivibrator 104. At the beginning of the applied pulse, assuming a rectangular waveform, multivibrator 104 is immediately triggered so that its 0 output goes low. Line 114 is high at this time by reason of the high condition of the output of multivibrator 111. Assuming that the applied pulse terminates before the end of the time interval established by multivibrator 104, the output of OR gate 108 goes high, and triggers multivibrator 111 so that its output goes low. The output of multivibrator 110 remains low. Therefore, the condition of line 114 remains high, which is its normal condition.

A second possibility may occur as a result of a capsule which is partially filled at both ends but which has a gap at some point intermediate its ends. Two short pulses are produced at line 98 having a gap between them. At the end of the first short pulse, the output of gate 108 goes high and triggers multivibrator 111. The low condition of the output of multivibrator 111 holds gate 112 in a disabled condition so that line 114 remains high even though multivibrator 110 is triggered as a result of the return of multivibrator 104 to its stable condition during the second of the short pulses.

Under normal circumstances, the duration of the applied pulse exceeds the time interval established by multivibrator 104. The output of multivibrator 104 will be high at the same time that the output of Schmitt trigger 102 is high. This will produce a high at the output of AND gate 106 which will trigger multivibrator 110 so that its output goes high. This high and the high from multivibrator 111 will satisfy AND gate 112, and, two highs being present at the inputs of AND gate 112, a low is produced at output line 114, indicating a satisfactory capsule.

Returning now to FIG. 9, the outputs of the five delayed single shot multivibrators in group 96 are fed through negated inputs to a five input AND gate 116. The input lines are normally held positive by the connection of positive supply terminal 118 through resistors 120 to the lines. However, the output AND gate of each delayed single shot multivibrator includes a transistor which grounds the output line, thereby producing a low potential at the output line. When all of the five input lines to AND gate 116 are low, a high appears at its output which is connected to the data input "D" of a 12 bit shift register 122. An additional delayed single shot multivibrator 124 receives positive pulses which are produced as a result of the reflection of light from source 126 off a rotating marked disk 128 to phototransistor 130, the phototransistor being connected as a gate in a manner similar to the manner of connection of the phototransistors in array 88. The multivibrators in delayed single shot 124 are adjusted so as to produce a relatively short negative-going output pulse which normally occurs about half way between the beginning and end of the coincidence pulse produced at the output of AND gate 116. The output of multivibrator 124 is inverted, then delivered through line 132 to set input "S" of the shift register.

The shift takes place in shift register 122 whenever a positive-going pulse appears in line 132. Normally, the shift occurs when a high is present at the date input D. Consequently, the 1 outputs of the shift register normally remain in the high condition at all times. The 1 outputs are set to the high condition when positive supply voltages applied to the various supply terminals of the circuit by the application of a positive signal produced at that time by the circuit indicated at 134 to the present control terminal "PC" of the shift register.

The first two 1 outputs of the shift register are connected to the negated inputs of a two input OR gate 136. The second two 1 outputs of the shift register are connected to two of three negated inputs of a three input OR gate 138. The remaining 1 outputs of the shift register are similarly connected in pairs to three input OR gates 140, 142, 144 and 146. The third input of each of the three input OR gates is negated and connectable to ground through a rotary switch 148 which is so designed as to short successively closed contacts together. The outputs of all five OR gates are connected together through line 150 which is connected to an input of two input AND gate 152. The output of delayed single shot 124 is connected through line 154 to the other input of AND gate 152. The output of AND gate 152 is negated and connected to the input of a single shot multivibrator 156, the output of which is amplified by amplifier 158 to control indicator lamp 160.

Line 154 is also connected to an input of two input AND gate 162. The other input to AND gate 162 is derived from any one of four 0 output of shift register 122, the selection being made by switch 164, the wiper of which is connected through line 166 to AND gate 162. The negated output of AND gate 162 is delivered to single shot multivibrator 166, the output of which is amplified by amplifier 168 and used to operate valve solenoid 90.

The output of single shot multivibrator 156 not only controls indicator lamp 160, but is also connected through line 170 to an input of AND gate 172. The other input is connected through resistor 174 to the positive supply, a reset switch 176 being provided to produce a low momentarily to this input. The negated output of AND gate 172 is connected to an input of two input AND gate 178, the other input of which is derived from the negated output of three input AND gate 180, AND gates 178 and 180 are interconnected in a latch configuration. One of the other inputs of AND gate 180 is derived from the negated output of AND gate 178. The third input of AND gate 180 is derived through line 182 from circuitry 134 so that a positive pulse is delivered to a third input when power is applied to the monitoring circuitry. The output of the latch at the output of AND gate 178 is amplified by amplifier 184 and used to operate halt solenoid 92.

The operation of the solenoid valve 90 of the reject mechanism is effected after a delay whenever a condition occurs such that the clock pulse appears at shift register set terminal S when the data terminal is in a low condition. A high travels along the 0 output of the shift register until it reaches the 0 output to which line 166 is connected through switch 164. With line 166 temporarily in a high condition, the reappearance of a high in line 154 following the clock pulse results in the production of a low at the output of AND gate 162. This low triggers multivibrator 166, and effects opening of the solenoid valve which delivers a blast of air to reject nozzle 56 (FIG. 2), thereby removing a defective card from the conveyor. The shift register produces the necessary delay to allow the card to travel from the point of which it is inspected by inspection head 42 to the point where it is rejected by reject mechanism 56. Switch 164 (FIG. 9) allows the operator to make an electrical adjustment of the delay to insure that the blast of air occurs when the unacceptable card is in the optimum position with respect to the nozzle for reliable rejection.

OR gates 136-146 are arranged so that a high is produced in line 150 whenever at least one input of each of the gates is low. By the adjustment of switch 148, an artificially produced low can be effected at inputs of up to five of the six OR gates. For example, with switch 148 in the position shown, a high in line 150 will be produced only when six consecutive unacceptable cards (having two rows each) are sensed by the inspection head. In the event of six unacceptable cards, there will be at least one low at the inputs of each of the six OR gates.

If switch 148 is moved one position clockwise, at least five consecutive unacceptable cards are necessary to produce a high in line 150. Switch 148 can be adjusted so as to produce a high in line 150 for any number of consecutive unacceptable cards between one and six.

When line 154 goes high at the end of a clock pulse, if line 150 is high, a low at the output of AND gate 152 triggers single shot multivibrator 156. The output of multivibrator 156 causes illumination of indicator lamp 160 and also produces a high in line 170 which results in a low at the output of AND gate 172. This low latches the interconnected AND gates 178 and 180 to a condition such that the output of AND gate 178 goes high and effects operation of halt solenoid 92. Halt solenoid 92 halts operation of the capsule packaging machinery by effecting disconnection of electric motive power. Resetting of the latch is effected by momentary closure of switch 176 which delivers a low through line 186 to an input of AND gate 180. The output of AND gate 180 goes high, and since both inputs of AND gate 180 are high at this time, its outputs go low and halt solenoid 92 is deenergized. Thus, the operator can cause operation of the packaging machine to resume by momentary operation of switch 176.

The operation of the electrical circuitry in FIG. 9 may be briefly summarized as follows.

The occurrence of an inadequately filled capsule is sensed by the comparison of the time through which its contents block the inspection beam with a time interval which is electrically predetermined by the parameters of the components of a multivibrator corresponding to monostable multivibrator 104 (FIG. 10). These parameters may be adjusted to set the criteria for acceptability, and also to accommodate the operating speed of the packaging machinery, which, of course, determines the interval through which the inspection beam is blocked for a given quantity of capsule contents.

All of the capsules in a row are inspected simultaneously, and the circuitry effects a rejection of the card if any capsule in any row on the card is unacceptable because of inadequate contents.

When all of the capsules in a row are aligned, the pulses produced by the delayed single shot multivibrators in group 96 coincide. However, if a capsule is badly misaligned with the remaining capsules in its row, the pulse corresponding to it will not coincide with the other pulses, and no coincidence pulse will be produced at the output of AND gate 116. The card carrying the misaligned capsule will be rejected. The extent of misalignment which will be tolerated is determined by the lengths of the pulses produced at the outputs of the delayed single shot multivibrator, and these lengths may be adjusted.

The row itself must be located within certain limits measured in the direction of travel of the backing strip since otherwise rows of capsules might be positioned too close together or too far apart on a card. The pulse produced by delayed single shot 124 is synchronized with the packaging machinery, and insures the rejection of any card in which a row is so far out of proper position that the coincidence pulse at the output of AND gate 116 does not overlap the pulse at the output of delayed single shot 124. The length of the pulse produced by delayed single shot 124 may be adjusted electrically, and its position may be adjusted either electrically or mechanically.

Switch 164 provides for especially simple and convenient adjustment of the delay between inspection and rejection.

Switch 148 establishes the criteria for causing the packaging machinery to stop automatically. Generally speaking, the apparatus senses the frequency of unacceptable cards and causes the packaging machinery to halt when the frequency of unacceptable cards and causes the packaging machinery to halt when the frequency of unacceptable cards becomes too high. More specifically, the apparatus makes use of the shift register to effect a halt when a predetermined number of unacceptable cards in a row in produced. Various other means for effecting a halt of the packaging machinery when the frequency of unacceptable cards becomes too high will occur to those skilled in the art.

Similarly, other modifications may be made to what is specifically disclosed without departing from the scope of the invention as defined in the following claims.

I claim:
1. A quality control monitor for medicinal capsule packaging apparatus in which transparent capsules are filled with medication and fastened to a moving reflec- tive backing strip in rows which are transverse to the direction of movement of the backing strip, comprising:
- a plurality of light beam producing means, one for each capsule in a row,
- a plurality of photosensitive detectors, one for each capsule in a row, and
- means for mounting the light beam producing means and the photosensitive detectors for substantially simultaneous inspection of the capsules in a row, so that each beam approaches the backing strip at an oblique angle and is reflected to a different one of the detectors and so that each plane defined by the approaching and reflected part of a beam intersects the plane defined by the movement of a row of capsules to define a line which is oblique with respect to the direction of motion of the rows of capsules,
- whereby a relatively large number of pairs of light beam producing means and photosensitive detecting means are accommodated in a small row-wise space.

2. A quality control monitor according to claim 1 in which the means for mounting the light beam producing means and the photosensitive detectors comprises means for securing said light beam producing means and photosensitive detectors in fixed relationship to each other, and means for adjusting the distance between said securing means and the reflective backing strip.

3. A quality control monitor according to claim 1 in which the means for mounting the light beam producing means and the photosensitive detectors is a block having a plurality of substantially cylindrical passages for mounting said light beam producing means and detectors, the axis of each passage for mounting a light beam producing means intersecting the axis of a different passage for the mounting of a detector, the intersections being located substantially in a line external to the block and the planes defined by the intersecting axes intersecting the plane defined by the movement of a row of capsules to define lines which are oblique with respect to the direction of motion of the rows of capsules.

* * * * *